(12) United States Patent
Raasch

(10) Patent No.: US 6,942,342 B2
(45) Date of Patent: Sep. 13, 2005

(54) CLINICAL REFRACTIVE INSTRUMENTS

(75) Inventor: Thomas W. Raasch, Upper Arlington, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 10/210,262

(22) Filed: Aug. 1, 2002

(65) Prior Publication Data

US 2003/0030774 A1 Feb. 13, 2003

Related U.S. Application Data

(60) Provisional application No. 60/309,374, filed on Aug. 1, 2001.

(51) Int. Cl.⁷ .................................................. A61B 3/10
(52) U.S. Cl. ..................................................... 351/216
(58) Field of Search ............................... 351/205, 211, 351/212, 216, 217, 218, 221, 222, 239, 241, 243, 246

(56) References Cited

U.S. PATENT DOCUMENTS

| | | |
|---|---|---|
| 3,822,932 A | 7/1974 | Humphrey .................... 351/17 |
| 4,917,480 A | 4/1990 | Kato et al. ................... 351/211 |
| 6,467,906 B1 * | 10/2002 | Alpins ......................... 351/212 |

* cited by examiner

*Primary Examiner*—George Manuel
(74) *Attorney, Agent, or Firm*—Calfee, Halter & Griswold LLP (57) ABSTRACT

A clinical refractive instrument is described for adjusting dioptric power according to three orthogonal axes. The instrument includes a viewing aperture, a plurality of spherical lenses and a pair of cylindrical lenses. The plurality of spherical lenses are adjustable such that a selected spherical lens may be aligned with the viewing aperture. The pair of cylindrical lenses are operative to produce a combination of astigmatic power elements $J_0$ and $J_{45}$. Each of the cylindrical lenses capable of being independently rotated, and the pair of cylindrical lenses may be super imposed with respect to each other and aligned with the viewing aperture and the selected spherical lens. Methods for using and controlling the instrument are also described.

15 Claims, 5 Drawing Sheets

Three-dimensional dioptric space

Vector addition of component crossed cylinders in the plane of astigmatism

CLINICAL REFRACTIVE INSTRUMENTS

CROSS-REFERENCE TO RELATED APPLICATIONS

This application claims priority to U.S. Provisional Application Ser. No. 60/309,374 filed Aug. 1, 2001 which is hereby incorporated by reference in its entirety.

TECHNICAL FIELD

The present invention generally relates to optomechanical ophthalmic diagnostic instruments. More particularly, the present invention relates to novel subjective refractors or phoropters with unique and advantageous capabilities, and similar instruments used to perform subjective refractions.

BACKGROUND

Phoroptors, also known as subjective refractors, are used in most eye examinations to measure refractive error (e.g. nearsightedness, astigmatism). Subjective refractors are used to refract, or bend, the light entering the eye, modifying its focus and thus the sharpness of the image formed on the retina. The clarity of focus is reported by the subject, hence the name subjective refractor. Systematic procedures are required for the accurate determination of nearsightedness (myopia) or farsightedness (hyperopia), and astigmatism. These procedures involve manipulation of the lens powers by the examiner, and repeated questioning of the subject, e.g. "which is better, lens 1 lens 2?".

Conventional instruments employ spherical and cylindrical lenses, and a particular spherocylindrical power can be achieved by appropriate selection of sphere power, cylinder power, and cylinder axes. A significant problem with conventional instruments, however, is that complicated instruments and clinical procedures are required to reliably converge on the endpoint. Conventional refractors incorporate 10 or more separate cylindrical, or astigmatic, lenses. In addition, each of these lenses must be rotatable through at least 180°. These instruments and procedures are necessary due to the non-orthogonal nature of the conventional measures of dioptric power—sphere, cylinder, and axis. When either cylinder power or axis is changed, the spherocylindrical power does not change along just one dimension.

An analog of a conventional phoroptor is a slide projector with three focus knobs. Each of the three knobs must be set to the correct position for optimum focus. The non-orthogonality of sphere, cylinder, and axis means that as one knob is adjusted, the optimum position for one or both other knobs also changes. Consequently, clinical refraction with a conventional instrument requires systemic procedures to check and re-check sphere, cylinder and/or axis in order to reliably converge on the final endpoint.

Spherocylindrical dioptric powers are conventionally represented by a sphere power, a cylinder power, and a cylinder axis. These three parameters are not independent, and this may lead directly to a number of difficulties. The most often recognized instance of non-independence is the non-zero spherical equivalent power of a cylindrical lens.

An alternative representation of spherocylindrical power has significant advantages. This alternative representation has been rapidly gaining recognition in recent years, although it appeared in the literature some 30 years ago. As with other rapidly developing fields, new terminology has proliferated, which sometimes lacks consistency with that of others, and fails to identify overlap or relationships between terms of different sets. For simplicity, this application adopts the terminology first used by L. N. Thibos, W. Wheeler and D. Homer in "Power vectors: An application of fourier analysis to the description and statistical analysis of refractive error," *Optom Vis Sci* 74(6): 367–75 (1997).

Wheeler and Homer described spherocylindrical dioptric power as consisting of a spherical equivalent (or mean power, M), and two components of astigmatism, $J_0$ and $J_{45}$. These two terms get their particular names because they can be represented by Jackson crossed cylinders with axes at 0°/90° and 45°/135°, respectively. These two astigmatic components define a plane of astigmatism, with the $J_0$ and $J_{45}$ axes corresponding to the x- and y-axes. The mean power line, M, is perpendicular to this plane of astigmatism, so together the three axes define a three-dimensional space, within which exists every spherocylindrical dioptric power.

Figure 1:
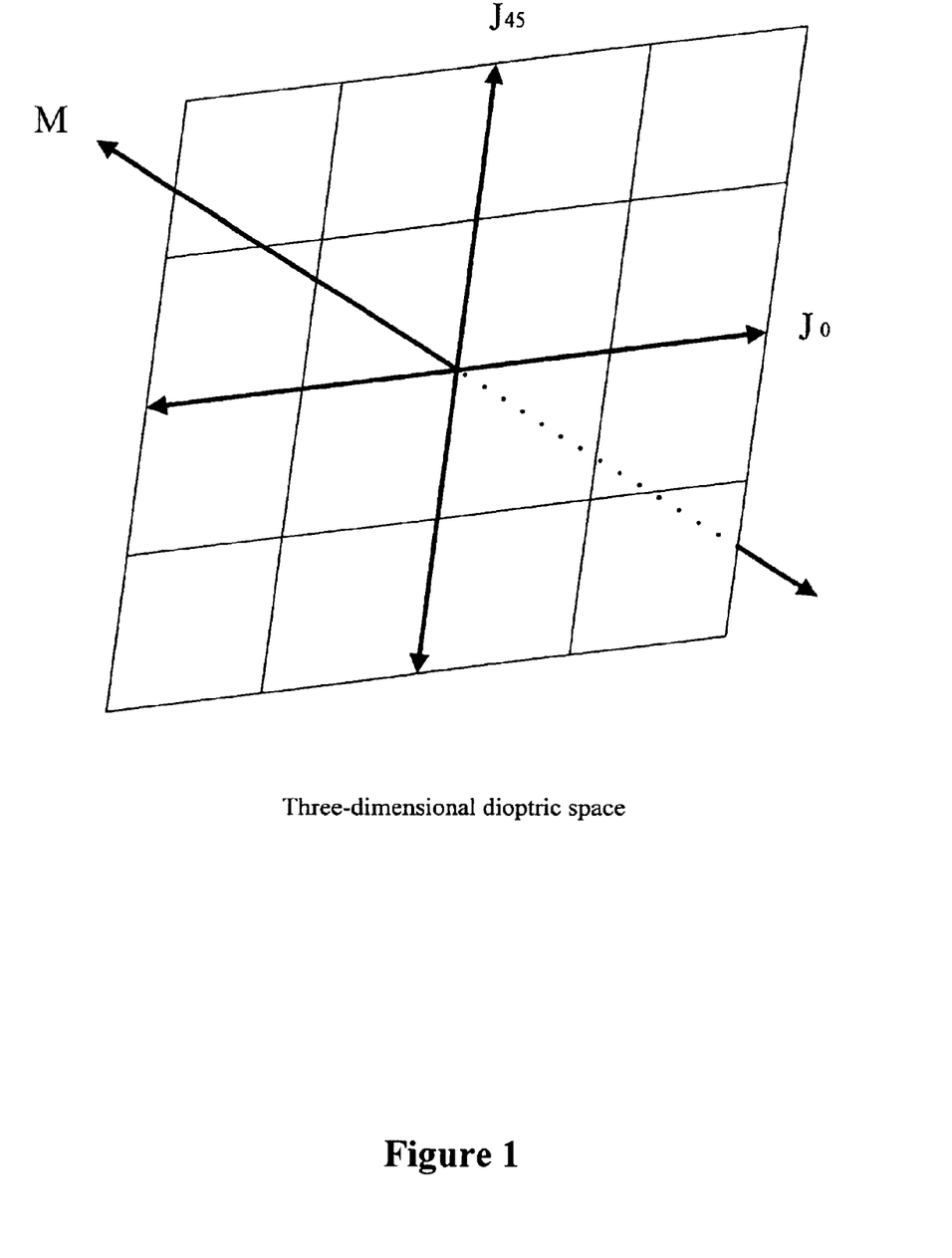
FIG. 1 is a perspective view of dioptric space, defined by three orthogonal axis: M, $J_0$ and $J_{45}$.

FIG. 1 illustrates this three-dimensional dioptric space, defined by the three orthogonal axes, M, $J_0$, and $J_{45}$. The units along each of these three axes are diopters, and each point within this space is a unique spherocylindrical power.

The arithmetic relationships of sphere, cylinder, and axis, to M, $J_0$, and $J_{45}$ are straightforward. They are:

$$M = Sph + Cyl/2 \tag{1}$$

$$J_0 = -\frac{Cyl}{2} \times \cos(2 \times Axis) \tag{2}$$

$$J_{45} = -\frac{Cyl}{2} \times \sin(2 \times Axis) \tag{3}$$

M is simply the usual spherical equivalent, or mean power of the system. After doubling the axis, $J_0$ and $J_{45}$ are the projections of half the cylinder power onto the x- and y-axes of the plane of astigmatism.

Converting from M, $J_0$, and $J_{45}$ to Sph, Cyl and Axis:

$$Sph = M + \sqrt{J_0^2 + J_{45}^2} \tag{4}$$

$$Cyl = -2 \times \sqrt{J_0^2 + J_{45}^2} \tag{5}$$

$$Axis = \frac{\tan^{-1}\left(\frac{J_{45}}{J_0}\right)}{2} \tag{6}$$

Attempts to improve upon conventional phoroptors have been described or produced in the past. One such instrument, described in "A Remote Subjective Refractor Employing Continuously Variable Sphere-Cylinder Corrections" by William E. Humphrey, *Optical Engineering*, 15, 286–291 (1976) and in U.S. Pat. No. 3,927,933 to William E. Humphrey, used special lenses described in "Development of variable focus lenses and a new refractor" by Luis E. Alvarez, *Journal of the American Optometric Association*, 49, 24–9 (1978) and in U.S. Pat. No. 3,507,565 to Luis E. Alvarez and William E. Humphrey to provide astigmatic decomposition.

Conventionally, astigmatism is expressed, and measured, in polar coordinates, i.e. having a magnitude (or amount), and an orientation (or direction). Astigmatic decomposition expresses astigmatism in Cartesian coordinates, i.e. having X- and Y-axis values. An instrument that implements astigmatic decomposition simplifies the measurement of astigmatism, with the same or better accuracy as compared to conventional instruments.

Measurement of astigmatism employing astigmatic decomposition simplifies the measurement because the two values (X and Y) of astigmatism are independent, unlike the conventional means of measuring it in polar coordinates. That is, because the X and Y astigmatism values are independent, they do not interact during measurement, in contrast to the conventional method, wherein changing one value affects the optimum value of the other.

In addition, a feature which distinguishes such an instrument from conventional instruments is that the two components of astigmatism are independent of the sphere (i.e. the correction for nearsightedness or farsightedness). This type of instrument may be referred to as a vector refractor, owing to the vector representation of spherocylindrical powers.

Humphrey's instrument was not a commercial success, despite its unique features. Contributing factors included the size of the machine, which usually required a dedicated room; expense—the machine performed similar functions to other instruments that cost $1/10^{th}$ as much; lack of understanding of the theory and operation of the instrument; and the necessity for re-training of office staff and re-arrangement of office routine.

Other instruments have been described which implement astigmatic decomposition with two pairs of counter-rotating cylindrical lenses (i.e. "Stokes" lenses) (U.S. Pat. No. 3,822,932 to Humphrey et al and U.S. Pat. No. 4,943,162 to Sims) The Sims system had many of the same problems as the Humphrey instrument. It used astigmatic decomposition, but did so with five lenses per eye (more complexity/moving parts), and could only operate in "astigmatic decomposition" mode.

There have also been important developments in objective refractors and autorefraction. Autorefractors, however, have not eliminated the need for subjective refractors. At the very least, the results of subjective refraction serve as the final verification of a refractive procedure, regardless of how the preliminary refraction was performed. In addition, subjective refraction actively involves the patient in the process of arriving at a refractive correction. That fact alone does, to some degree, elevate the importance of subjective refraction, and confers upon it a level of legitimacy in the eyes of the examiner and the patient, which is not gained through objective refraction.

SUMMARY OF THE INVENTION

The present invention provides physical lens systems that conform to the three orthogonal axes of this dioptric power space. In other words, the lens systems of the present invention permit changes of the dioptric power along any one of the three axes, independent of the other two axes. The novel instruments described herein implement lens powers along these three orthogonal axes.

Instruments embodying the present invention may retain the functionality of conventional phoroptors, with flexible manipulation of the vergence, or focus, of light as it enters the eye so that the refractive error or eyeglass prescription can be determined. In addition, the instruments embodying the present invention support the use of astigmatic decomposition elements, which enables more efficient and accurate determination of refractive error. The astigmatic decomposition is implemented in a novel way. Spherical and astigmatic powers are manipulated independently. Thus, the instruments of this invention, unlike conventional systems, provide stereocylindrical power in three components that are substantially mathematically orthogonal. Mathematical orthogonality means that the three values that define the correction for refractive error are independent of each other. That is, the value for one can be determined without introducing errors in the other two. This characteristic is not present in conventional instruments.

The current invention eliminates the need to incorporate a full range of cylindrical lenses. It does so by implementing astigmatic powers with a single pair of rotating superimposed cylindrical lenses of equal magnitude. This reduces the mechanical complexity of the instrument, and the number of lenses through which the patient must view. This in turn reduces other potential problems with more moving parts, multiple surfaces which produce more reflections and light loss, and cleaning and maintenance requirements. A specific cylinder power and axis can be produced by appropriate selection of the orientation of these two lenses. This eliminates the need for the 10 or more cylinder lenses, but also enables selection of lens powers with much greater precision, rather than in discrete power steps with conventional instruments. Computer control of lens orientation also permits more flexible use of the refractor, i.e. in either "conventional" mode, or in "vector" mode. This is not implemented or described in previous refractor designs.

According to a first aspect of the present invention, a clinical refractive instrument is disclosed for adjusting dioptric power according to three orthogonal axes. The instrument includes a viewing aperture, a plurality of spherical lenses associated with the viewing aperture, and a pair of cylindrical lenses associated with the viewing aperture.

The plurality of spherical lenses are adjustable such that a selected spherical lens of the plurality may be aligned with the viewing aperture. The pair of cylindrical lenses associated with the viewing aperture are operative to produce a combination of astigmatic decomposition elements $J_0$ and $J_{45}$. The pair of cylindrical lenses are super imposed with respect to each other and aligned with the viewing aperture and the selected spherical lens. Each of the cylindrical lenses is capable of being independently rotated.

According to a second aspect of the present invention, a method for adjusting a clinical refractive instrument is disclosed. The method includes establishing an initial dioptric power. The method also includes providing a first target having vertical and horizontal contours, and adjusting a $J_0$ component to equalize the relative clarity of the vertical and horizontal contours. The method further includes providing a second target having counter-diagonal contours, and adjusting a $J_{45}$ component to equalize the relative clarity of the counter-diagonal contours. In addition, the method includes adjusting a spherical power component.

According to a third aspect of the present invention, a method for controlling a clinical refractive instrument is disclosed. The method includes determining a selected dioptric power setting. A spherical lens is selected based on the selected dioptric power setting and positioned in alignment with the a viewing aperture. Further, the orientation of a pair of cylindrical lenses is determined based on the selected dioptric power setting, and the orientations of the pair of cylindrical lenses are effected to produce the selected dioptric power.

BRIEF DESCRIPTION OF THE DRAWINGS

For a more complete understanding of the present methods and systems, reference is now made to the following description taken in conjunction with the accompanying drawings in which like reference numbers indicate like features and wherein.

DETAILED DESCRIPTION

Figure 2:
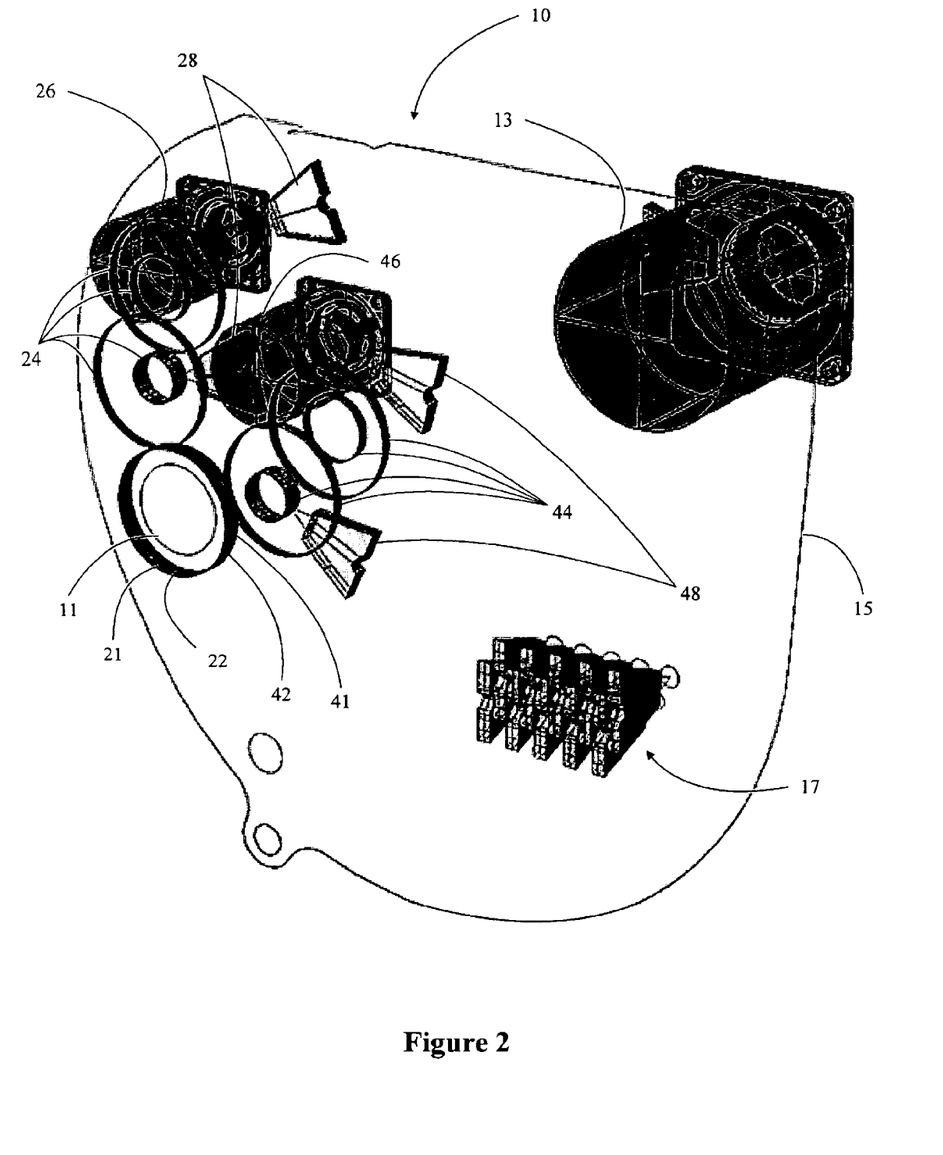
FIG. 2 is an exploded perspective view of certain elements in a phoropter embodying this invention.

Referring to FIG. 2, there is illustrated one half of a phoropter, generally referred to as 10. The components illustrated in FIG. 2 are replicated in a mirror image that comprises the right half of the instrument.

The substrate for one embodiment of this invention may be a Greens refractor. This instrument is relatively easy to deconstruct while preserving some necessary functions, such as the sphere wheel and interpupillary distance adjustment mechanisms. The front face of the instrument supports the original cylinder lens mechanism. This original front is discarded, and a new front is fabricated, together with the crossed cylinders, gears, and stepper motors to implement the astigmatic powers.

Phoropter 10 is equipped for conventional refractive measurements. The phoroptor contains a viewing aperture 11 through which the patient or subject views a chart or other target. A series of spherical lenses (not shown) mounted on a wheel contained within the body of the instrument are rotated into position within the aperture 11 by a stepping motor 13 and drive belt 15. Alternatively, a continuously variable spherical lens, such as the Alvarez lens could be used as an equivalent to the series of spherical lenses.

Stepping motor 13 preferably has 200 1.8 deg steps per rev, so that ½ rev of motor –>1 step of the sphere wheel. Sensors 17 determine the position of the wheel and, thereby, the power of the lens aligned with the aperture. This information is recorded by a computer (not shown) as a measure of the patient's myopia or hyperopia.

In the example embodiment, a pair of cylinder lenses 21, 41, also mounted within aperture 11, are used to determine astigmatism. Jackson Cross Cylinder lenses with principal meridian powers of –2.50 D and +2.50 D, in plano-saddle form are preferred. Although Jackson Crossed Cylinders are illustrated, other pairs of cylindrical lenses of equal magnitude in power could also be used. These lenses are capable, in combination, of producing a cylindrical power from zero to 10 DC at any orientation. The orientation of these two lenses are controlled by stepper motors 26 and 46.

Like the Humphrey instrument described above, the novel subjective refractors of this invention feature astigmatic decomposition, but they operate in a fundamentally different way, and thereby avoid problems that led to the failure of the Humphrey instrument. The new instrument is similar in appearance to a conventional instrument, being similar in size and physical configuration, and being mounted on the same type of adjustable arm. Importantly, it can also operate as a conventional instrument, unlike the Humphrey instrument. This capability facilitates incorporation of the instrument into clinical use. The full capabilities of the instrument, i.e. those that exploit astigmatic decomposition, can then be incorporated as the operator becomes familiar with that functionality.

Lenses 21 and 41 are superimposed, i.e. coaxial and mounted face to face, and independently adjustable in orientation. Each lens has a ring of teeth 22, 42 around its outer edge, and is rotated by a series of gears 24, 44 and a stepping motor 26, 46, preferably a motor with 200 steps per 360 degree revolution. Sensors 28, 48 detect marked locations on the gears and/or lenses, and thereby the orientation of lenses 21 and 41, which is recorded by the computer mentioned above. The orientation of the two lenses results in a specific cylindrical power, which can be recorded and displayed either in conventional terms (i.e. as a power and an axis), or in terms of the X and Y values in Cartesian coordinates.

The resolution in astigmatic lens powers available with this lens system is a function of the powers of the component crossed cylinders and the angular resolution in their orientation. The instrument incorporates ±2.50 D crossed cylinders, and stepper motors with angular resolution of 200 positions per revolution. The preferred gearing mechanism provides 800 positions per revolution of the lenses, and this becomes 400 unique orientations of each lens (because cylinder lenses have a 180° cycle). These parameters result in the minimum astigmatic power (other than zero) of 0.04 D (or 0.08 DC in clinical terms), with angular resolution in axis of 0.45°. Finer resolution astigmatic powers could be achieved with lower power component crossed cylinders (at the expense of power range), or with different stepper motor/gearing systems to permit a greater number of unique lens orientations.

The improved vector refractors of this invention have some similarities to the instruments of Humphrey and Sims, but they also have important differences. Astigmatic powers are produced with paired Jackson Cross Cylinder ("JCC") lenses. This is similar to a Stokes lens, although unlike a Stokes lens, the two lenses are free to rotate to an arbitrary orientation, independent of the other's orientation. By appropriate selection of the orientation of each lens, a particular astigmatic power can be produced. Employing this lens system, a spherocylindrical power is produced with three lenses: the sphere lens to produce M, and two JCC lenses, oriented to achieve the desired $J_0$ and $J_{45}$ values.

As noted above, the orientation of the two lenses is controlled by stepper motors, which are computer or microprocessor-controlled. The range of astigmatic powers achievable is a function of the power of the two component crossed cylinders. This vector refractor employs ±2.50 D crossed cylinders. With the motors and gearing of this instrument, each lens can be rotated to 400 unique orientations per 180°. A pair of these lenses can then produce a power from plano to 5.00 diopters of astigmatic power (or in conventional terms, plano to 10.00 DC of cylinder power). These crossed cylinder lenses were chosen to maximize the power range of the instrument, while providing sufficient resolution in power. The lowest power possible with this exemplary design is less than 0.10 D of astigmatic power, and the cylinder axis orientation resolution is 0.9°.

Figure 3:
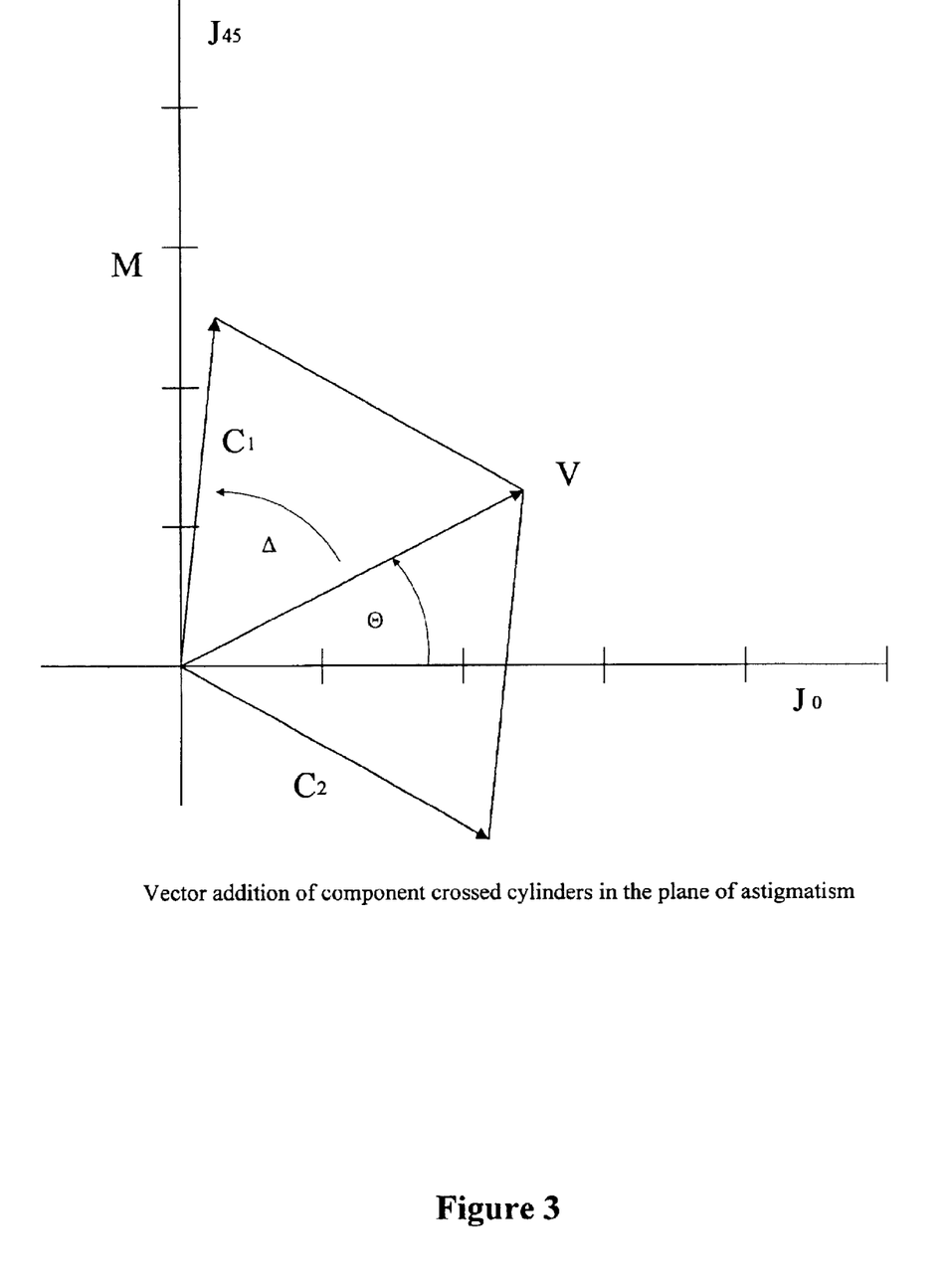
FIG. 3 illustrates vector addition of component crossed cylinders in the plane of astigmatism.

FIG. 3 illustrates vector addition in the plane of astigmatism to produce an astigmatic power. The vector, V, is the sum of the two component vectors, $C_1$ and $C_2$. $C_1$ and $C_2$ are of constant magnitude (determined by the power of the JCCs), but change in orientation as the JCCs are rotated. $C_1$ and $C_2$ are oriented to produce the vector V:

$$V = \begin{bmatrix} J_0 \\ J_{45} \end{bmatrix} \tag{7}$$

where $J_0$ and $J_{45}$ are the x- and y-coordinates, respectively, in the plane of astigmatism.

The orientation of the vector is:

$$\Theta = \tan^{-1}\left(\frac{J_{45}}{J_0}\right). \tag{8}$$

The differential orientation, Δ, of the two component vectors on either side of Θ is:

$$\Delta = \cos^{-1}\left(\frac{|V|}{2C}\right), \quad (9)$$

where $|V|$ is the magnitude of the vector, $V$, and $C$ is the magnitude of the components $C_1$ and $C_2$. Therefore, in order to achieve any particular astigmatic power represented by $V=[J_0\ J_{45}]^T$, the orientations of the two component vectors in the astigmatism plane are:

$$\Theta+\Delta, \text{ and } \Theta-\Delta. \quad (10)$$

To convert those two orientations in the plane of astigmatism to actual orientation of the component JCC lenses, each angle is halved (a result of the 180° periodicity of cylindrical lenses). Therefore, to produce a power of, for example:

$$V = \begin{bmatrix} J_0 \\ J_{45} \end{bmatrix} = \begin{bmatrix} 2.0 \\ 0.75 \end{bmatrix}$$

The orientation of the vector in the plane of astigmatism is $$\Theta = \tan^{-1}\left(\frac{J_{45}}{J_0}\right) = \tan^{-1}\left(\frac{0.75}{2.0}\right) = 20.6°.$$

The differential rotation, $\Delta$, from $\Theta$ is (assuming JCC power of C=2.5 D) is:

$$\Delta = \cos^{-1}\left(\frac{|V|}{2C}\right) = \cos^{-1}\left(\frac{2.14}{5}\right) = 64.7°.$$

Consequently, the orientation of the (−) cylinder axes of the two component crossed cylinders is:

(20.6°+64.7°)/2=+42.7°, and (20.6°−64.7°)/2=−22.1° to produce an astigmatic power of $$V = \begin{bmatrix} 2.0 \\ 0.75 \end{bmatrix}.$$

Using equations (8), (9), and (10), any astigmatic power within the range of the lenses can be achieved. Together with the M component provided by the sphere wheel, any power in three-dimensional dioptric space can be produced.

The instrument is driven by software which controls the stepper motors and thereby the spherocylindrical powers produced by the lenses, and the implementation of routines that support clinical research studies and clinical refraction routines with the instrument. Software modules may also emulate conventional instruments, and implement other refraction routines and psychophysical methods.

Figure 4:
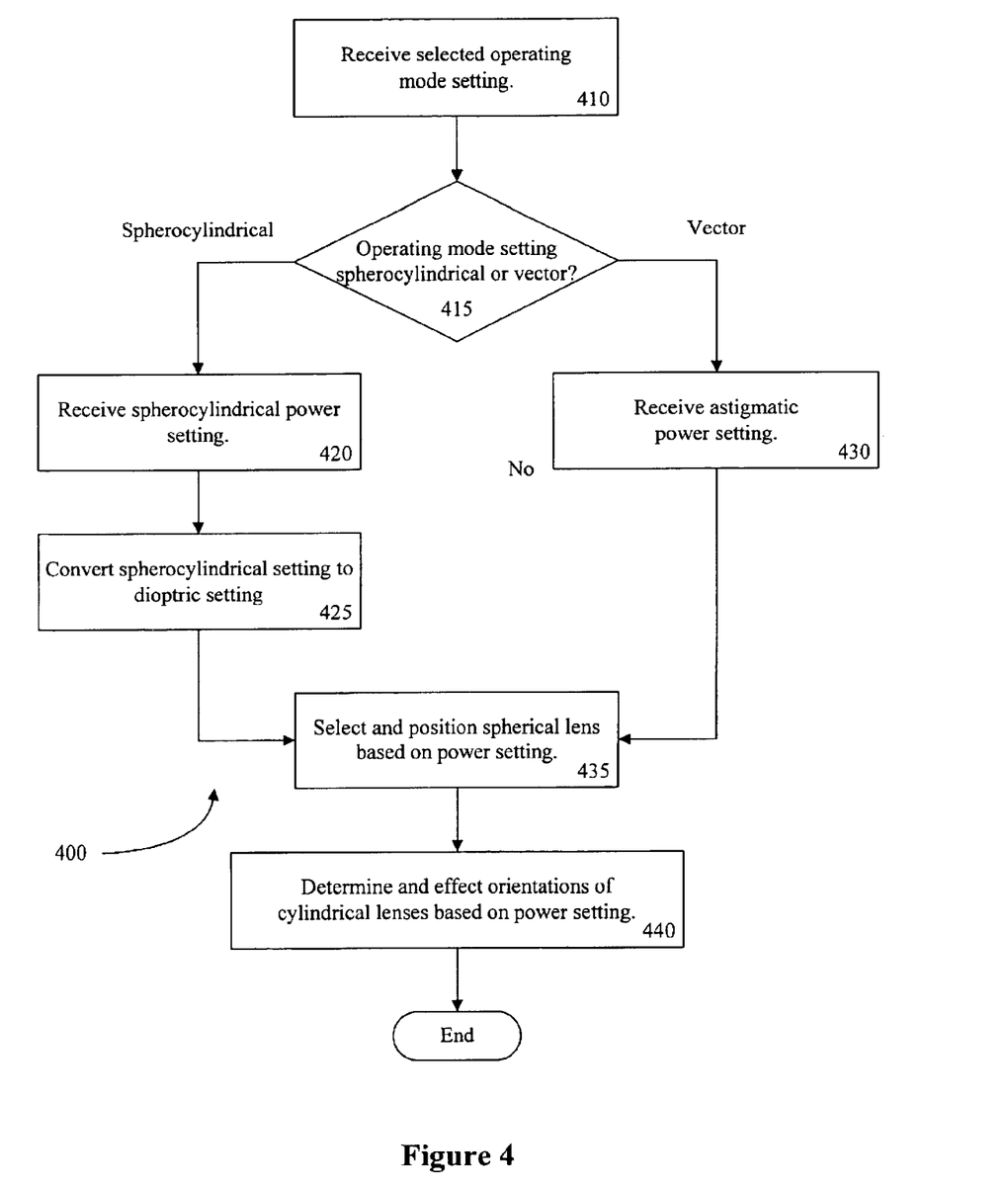
FIG. 4 illustrates an exemplary methodology for controlling a clinical refractive instrument.

Referring now to FIG. 4, an exemplary method for controlling a clinical refractive instrument 400 is illustrated. At block 410, a selected operating mode setting is received. In this embodiment, the refractive instrument may be operated in either spherocylindrical or dioptric modes, although other non-standard modes could be easily accommodated. Decision block 415 determines how the power setting is received. If the operating mode setting is spherocylindrical, spherocylindrical power components, sphere power, cylinder power and cylinder axes, are received at block 420, and converted into dioptric power components, M, $J_0$, and $J_{45}$ at block 425.

If the operating mode setting is vector, dioptric power components, M, $J_0$, and $J_{45}$ are received at block 430. At block 435, the dioptric power component M is used to select and position the appropriate spherical lens within the instrument. At block 440, the dioptric power components $J_0$, and $J_{45}$ are used to determine the appropriate orientations of the cylindrical lenses, and the cylindrical lenses are so oriented within the instrument.

This instrument enables a variety of questions to be explored and hypotheses to be tested. The instrument is very flexible in that a spherocylindrical power within the range of the instrument can be achieved, and arbitrary changes in lens power can be made through software control. For example, simulation of a flip crossed-cylinder, as typically used in astigmatic determination with a conventional instrument, can be implemented in the new instrument.

Under software control, the instrument can operate as a conventional phoroptor, i.e. changes in power can be made as though the changes were actually in sphere, cylinder, and cylinder axis. Similarly, the function of a flip crossed-cylinder can be produced without an actual flip crossed-cylinder. A flip crossed cylinder simply adds a $J_0$ and $J_{45}$ value to the astigmatic power, depending on the power and orientation of the crossed-cylinder. So flipping a flip crossed-cylinder is simply jumping from one location in the plane of astigmatism to another location. This function can easily be created with the new vector refractor.

This refractor can be used in two primary modes. First, it can emulate a conventional refractor. The operator would control the refractor through a control panel, and the desired astigmatic power and axis would be achieved through the appropriate orientation of each lens. A computer would perform the necessary calculations to determine the required lens orientations, and the lenses would be rotated to those orientations by stepper motors under the control of a computer. The interface through which the operator controls the computer reproduces the functionality of a conventional instrument. This instrument is mechanically simpler than a conventional refractor, as it has fewer moving parts. There are additional advantages of this design, e.g. the operator would not need to adjust sphere power to compensate for changes in cylinder power, as is required with a conventional refractor. Finally, operation in this mode would facilitate acceptance of this new instrument by clinicians. This could be an important factor, since most practitioners may be reluctant to embrace a new way to perform this fundamental part of a standard eye examination.

The other operating mode of this refractor, however, exploits an important feature of this instrument, giving it an important and unique advantage over conventional instruments. In this mode, astigmatic powers are "decomposed" into two orthogonal components. Instead of specifying astigmatism in terms of a power and axis (i.e. in polar coordinates), it is specified in terms of the power of two orthogonal components. This has the advantage that these two components are independent of each other, and independent of the sphere power. This property is not present with conventional instruments, and offers distinct advantages when performing a subjective refraction. This operating mode is referred to as "vector" mode, since the orthogonal components of astigmatism are conveniently represented mathematically as vectors. Operationally, in this mode the examiner would adjust the magnitude of the two components of astigmatism. This could be done in one of several ways, e.g. using a flip-cross-cylinder to implement a two-alternative forced choice, or "2AFC" procedure, or a method of adjustment ("MOA") procedure). Additionally, the patient him- or herself could perform a method of adjustment procedure by adjusting the magnitude of these components. It is not possible to arrive at an accurate endpoint using method of adjustment procedures using conventional instrumentation. Based upon data gathered from the first-generation prototype in a clinical study, any of these procedures could enable more efficient determination of refractive error, and do so with greater accuracy. The opportunity to perform this part of the eye examination more efficiently and accuracy represents the primary potential advantage of this instrument.

Two basic vector refractor routines were outlined above. The first is referred to as "Examiner 2AFC", because the examiner controls the refractor, and it employs a form of a two-alternative forced choice task using a flip crossed cylinder. The purpose of a flip crossed cylinder is, in general, to permit a 2AFC psychophysical task in astigmatic determination. With this new instrument, more flexible and intelligent search routines can be implemented, because astigmatic power changes can be made arbitrarily, and not be subject to limitations in power changes imposed by the particular flip crossed cylinder in use. For example, a 2AFC procedure could be implemented in which the most likely location of the correcting astigmatic power was sought. This is not unlike maximum likelihood procedures that are now incorporated into the software of some automated visual field instruments.

In a 2AFC paradigm for astigmatic determination, the two stimuli will be two locations in the plane of astigmatism. Those locations can be selected such that the patient response will provide the maximum reduction in uncertainty of the current estimate of the correcting astigmatic power. In general, those two locations in the plane of astigmatism will straddle the current estimate of the correcting astigmatic power. The size of the straddle can be made to adapt to the level of uncertainty.

The second routine featured adjustment by the patient. There is no fundamental reason why a patient, given control over $J_0$ and $J_{45}$, cannot converge accurately on the correct value for each. Study results suggest that this procedure is at least as repeatable as examiner-controlled procedures.

This lens system invites the use of special targets, which may aid in performing subjective refractions. Spherical defocus, of course, blurs contours of all orientations. Astigmatic defocus affects different orientations differentially. If the $J_0$ component is not optimally focused, then there will be, in general, differential blur of horizontal vs. vertical lines. The $J_0$ component can be brought into correct adjustment by equalizing the focus (or blur) of the horizontal and vertical lines. The $J_{45}$ component, if it is misadjusted, will also contribute blur to the horizontal and vertical lines, but that added blur from $J_{45}$ will be equal for the horizontal and vertical. Therefore, any differential blur of the horizontal and vertical lines is entirely a function of the $J_0$ component. The same is true of diagonal lines and the $J_{45}$ component.

Figure 5:
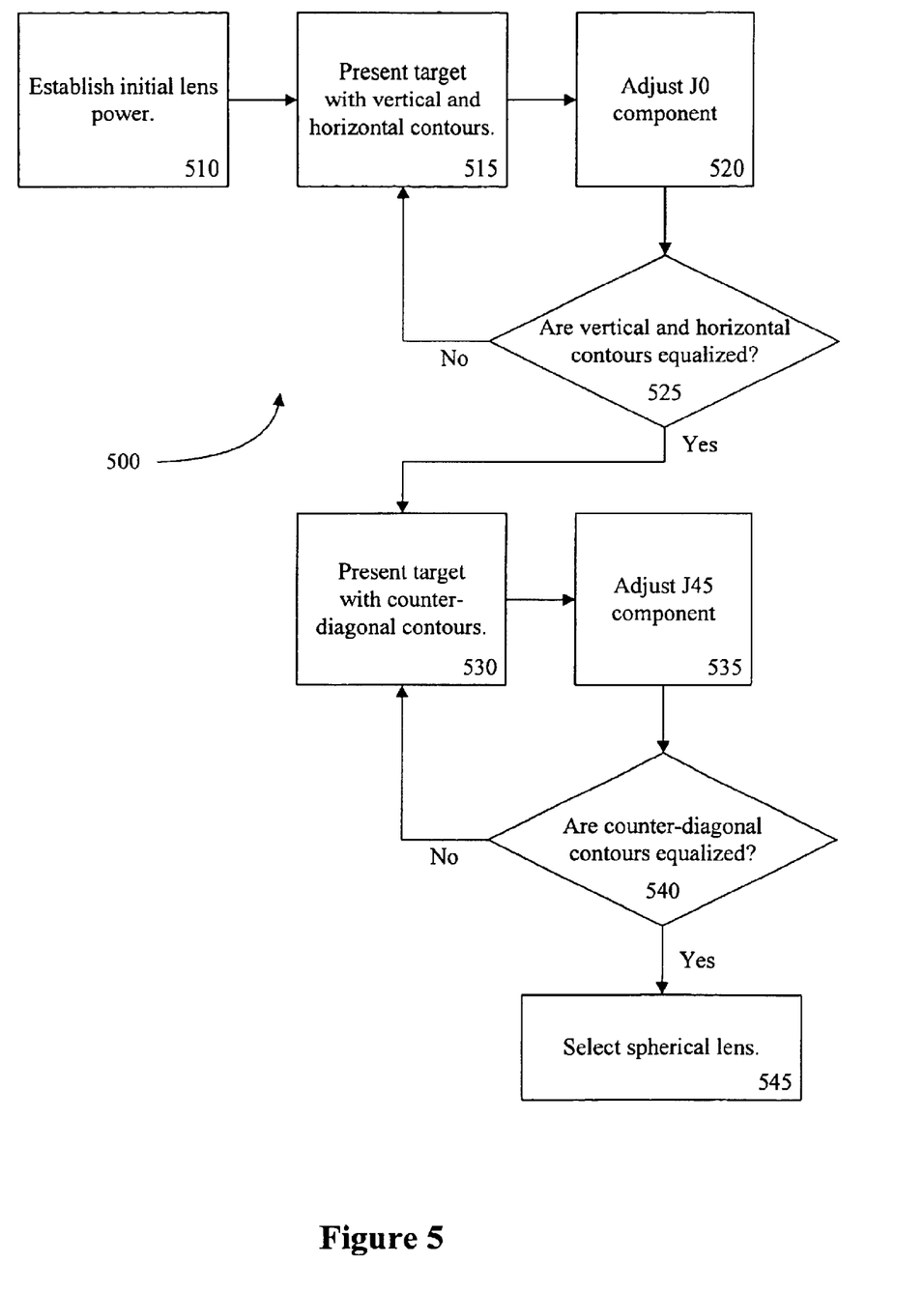
FIG. 5 illustrates an exemplary methodology for adjusting a clinical refractive instrument.

This schema can be exploited in subjective refraction procedures. One exemplary method of adjusting a clinical refractive instrument 500 is illustrated in FIG. 5. As shown, at block 510, an initial lens power is established. The initial lens power may be based on retinoscopy, previous refractive correction, or approximate spherical equivalent, for example. In one embodiment, the initial lens power may employ some predetermined lens power fogged with over-plus, by ~+0.50 DS.

At block 515, the patient is presented a target having only horizontal and vertical contours, such as a large "+", for example. The patient compares the relative clarity of the horizontal and vertical lines, and they are equalized at block 520 by adjusting the $J_0$ component. Decision block 525 provides that blocks 515 and 520 are repeated until the vertical and horizontal contours are equalized. Although equalized, the vertical and horizontal contours may still be blurred at this point due to the spherical and any existing $J_{45}$ blur.

At block 530, the patient is presented a target having only counter-diagonal contours, such as a large "X", for example. The patient compares the relative clarity of the counter-diagonal lines, and they are equalized at block 535 by adjusting the $J_{45}$ component. Decision block 540 provides that blocks 530 and 535 are repeated until the counter-diagonal contours are equalized. Although equalized, the counter-diagonal contours may still be blurred at this point due to the spherical blur.

At block 545, the spherical lens, the M component, is adjusted to eliminate any final blurring, and the resulting dioptric components represent a subjective measure of refractive error for the patient.

The vector approach to refraction may also be applied to settings in which phoroptors are not available or desirable. This may be the case in some vision screenings, in providing vision care to underserved populations (such as in humanitarian service projects in third-world areas), and in low vision refraction. In low vision refraction, for example, trial frame or over-refraction is typically preferred over the use of phoroptors, primarily because of the greater flexibility in the use of trial lenses. It is widely felt that it is difficult to arrive at a reliable endpoint in low vision refraction, it can be time-consuming, and it is difficult to train practitioners to an acceptable level of expertise, and to maintain that expertise. Procedures that derive from this vector refractor can be extended to low vision refraction, potentially improving on the efficiency, reliability, and accuracy of the procedure.

For low vision trial frame or over-refraction, a "Stokes" lens can help accomplish this. A candidate refraction routine could consist of the following steps:

Determine the best spherical refraction (or over-refraction), i.e. M.

Orient a Stokes lens in front of the eye to produce cylinder power, axis 180°/90° (i.e. the $J_0$ component). Use a method of adjustment to arrive at the $J_0$ power.

Provide correction for $J_0$ with a trial lens.

Orient the Stokes lens to produce $J_{45}$ power, and use a method of adjustment to determine this power.

Correct this power with a trial lens (or, combine the $J_0$ and $J_{45}$ powers into a single astigmatic lens oriented appropriately).

Refine M, $J_0$, and $J_{45}$.

Some computational support is useful. The necessary computations can easily be incorporated into a spreadsheet: the clinician enters the values found with the Stokes lens, and the spreadsheet calculations provide the correcting lens powers, orientations, and conventional spherocylindrical power specification, as needed. For maximum portability, these calculations may be stored in a programmable calculator or "PDA"-type device.

These trial lens procedures would be facilitated with JCC trial lenses. That is, rather than using (+) or (−) cylinder trial lenses, crossed-cylinders would aid in these trial lens refractions.

Similar procedures may facilitate refraction in other environments where phoroptors are unavailable or impractical. For example, students and faculty from most schools and colleges of optometry regularly embark on humanitarian trips to Latin America and Asia to provide vision and refractive care. Procedures as described above may improve on the efficiency and accuracy of these procedures. Various other applications, adaptations and modifications will be apparent to those skilled in the art, who should also realize that the foregoing descriptions are illustrative and are not meant to limit the scope of this invention. Accordingly, this application is intended to embrace such alterations, modifications, and variations that fall within the scope of the appended claims.

What is claimed is:

1. A clinical refractive instrument for adjusting dioptric power according to three orthogonal axes, comprising:
    a viewing aperture;
    a plurality of spherical lenses associated with the viewing aperture, the plurality of spherical lenses being adjustable such that a selected spherical lens of the plurality of spherical lenses may be aligned with the viewing aperture; and
    a pair of crossed cylindrical lenses associated with the viewing aperture operative to produce a combination of astigmatic power elements $J_0$ and $J_{45}$, the pair of cylindrical lenses super imposed with respect to each other and aligned with the viewing aperture and the selected spherical lens, each of the cylindrical lenses capable of being independently rotated.

2. The clinical refractive instrument of claim 1, further comprising:
    a pair of stepper motors, each stepper motor operative to control the orientation of one of the pair of cylindrical lenses.

3. The clinical refractive instrument of claim 2, wherein each cylindrical lens forms a series of teeth which cooperate with the respective stepper motor.

4. The clinical refractive instrument of claim 1, further comprising:
    a stepper motor operative to align the selected spherical lens with the viewing aperture.

5. The clinical refractive instrument of claim 1, wherein the plurality of spherical lenses are embodied as a continuously variable spherical lens.

6. The clinical refractive instrument of claim 1, further comprising:
    a pair of stepper motors, each stepper motor operative to control the orientation of one of the pair of cylindrical lenses;
    a stepper motor operative to align the selected spherical lens with the viewing aperture; and
    a processor operative to control the stepper motors to produce a selected dioptric power.

7. The clinical refractive instrument of claim 6, wherein the processor is operative to receive the selected dioptric power from an operator.

8. A method for adjusting a clinical refractive instrument, comprising:
    establishing an initial dioptric power;
    providing a first target having vertical and horizontal contours;
    rotating at least one lens of a pair of cylindrical lenses to equalize the relative clarity of the vertical and horizontal contours;
    providing a second target having counter-diagonal contours;
    rotating at least one lens of the pair of cylindrical lenses to equalize the relative clarity of the counter-diagonal contours; and
    adjusting a spherical power component.

9. The method of claim 8, wherein providing a first target includes providing a target substantially shaped like a "+".

10. The method of claim 8, wherein providing a second target includes providing a target substantially shaped like an "X".

11. The method of claim 8, wherein establishing an initial dioptric power includes determining a dioptric power and fogging the dioptric power with over-plus by approximately +0.50 DS.

12. A method for controlling a clinical refractive instrument, comprising:
    determining a selected dioptric power setting;
    selecting and positioning a spherical lens based on the selected dioptric power setting; and
    determining and independently effecting orientations of each of a pair of crossed cylindrical lenses based on the selected dioptric power setting.

13. The method of claim 12, wherein determining includes receiving astigmatic power components M, $J_0$ and $J_{45}$.

14. The method of claim 12, wherein determining includes:
    receiving spherocylindrical power components, sphere power, cylinder power and cylinder axes; and
    converting the spherocylindrical power components to astigmatic power components M, $J_0$ and $J_{45}$.

15. The method of claim 12, further comprising determining a selected operating mode, and wherein determining a dioptric power setting is performed based on the selected operating mode.

* * * * *